(12) United States Patent  
 Chancibot

(10) Patent No.: US 9,517,178 B2  
(45) Date of Patent: Dec. 13, 2016

(54) CARTRIDGE FOR SURGICAL FASTENERS WITH INTEGRATED LOCK SYSTEM

(75) Inventor: Arnaud Chancibot, Bazouges LaPerouse (FR)

(73) Assignee: Vitalitec International, Inc., Plymouth, MA (US)

( * ) Notice: Subject to any disclaimer, the term of this patent is extended or adjusted under 35 U.S.C. 154(b) by 150 days.

(21) Appl. No.: 14/114,274

(22) PCT Filed: Apr. 26, 2011

(86) PCT No.: PCT/US2011/033881  
 § 371 (c)(1),  
 (2), (4) Date: Oct. 28, 2013

(87) PCT Pub. No.: WO2012/148379  
 PCT Pub. Date: Nov. 1, 2012

(65) Prior Publication Data  
 US 2014/0054192 A1 Feb. 27, 2014

(51) Int. Cl.  
 *B65D 85/24* (2006.01)  
 *A24F 27/00* (2006.01)  
 (Continued)

(52) U.S. Cl.  
 CPC .............. *A61J 1/00* (2013.01); *A61B 17/1222* (2013.01); *B65D 75/326* (2013.01); *A61B 50/30* (2016.02); *B65D 2575/3245* (2013.01)

(58) Field of Classification Search  
 CPC .. A61J 1/00; B65D 75/326; B65D 2575/3245; A61B 17/1222; A61B 19/026  
 (Continued)

(56) References Cited

U.S. PATENT DOCUMENTS 3,713,533 A * 1/1973 Reimels ............. A61B 17/1222  
                   206/339  
4,294,355 A * 10/1981 Jewusiak ........... A61B 17/1222  
                   206/339

(Continued)

FOREIGN PATENT DOCUMENTS

CN     2568155     8/2003  
CN     2792501     7/2006  
(Continued)

OTHER PUBLICATIONS

Japanese Office action for Application No. 2014-508322 dated Jan. 13, 2015.

(Continued)

*Primary Examiner* — Nathan J Newhouse  
*Assistant Examiner* — Jennifer N Zettl  
(74) *Attorney, Agent, or Firm* — Bachman & LaPointe, PC

(57) ABSTRACT

A cartridge for holding surgical fasteners includes a base having a plurality of upstanding walls, adjacent pairs of walls defining spaces for holding surgical fasteners, at least one surgical fastener securing member movably connected to the base and movable relative to the base from an open position wherein fasteners can be loaded into the spaces, and a closed position wherein fasteners in the spaces are covered and held in the spaces, and a locking structure engageable between the base and the surgical fastener securing member for locking the surgical fastener securing member in the closed position.

11 Claims, 4 Drawing Sheets

(51) Int. Cl.
*A61J 1/00* (2006.01)
*A61B 17/122* (2006.01)
*B65D 75/32* (2006.01)

(58) Field of Classification Search
USPC ........ 206/138, 438, 339; 292/19, 80, 81, 87, 292/89, 91, 300, 303, 304; 606/143
See application file for complete search history.

(56) References Cited

U.S. PATENT DOCUMENTS

| | | | | |
|---|---|---|---|---|
| 4,361,229 A | * | 11/1982 | Mericle | A61B 17/122 206/339 |
| 4,936,447 A | * | 6/1990 | Peiffer | A61B 17/1222 206/339 |
| 4,961,499 A | * | 10/1990 | Kulp | A61B 17/1222 206/339 |
| 4,972,949 A | | 11/1990 | Peiffer | |
| 5,279,416 A | * | 1/1994 | Malec | B65D 25/10 206/339 |
| 5,908,430 A | * | 6/1999 | Appleby | A61B 17/1222 206/339 |
| 6,044,971 A | * | 4/2000 | Esposito | A61B 17/1222 206/339 |
| 6,273,253 B1 | * | 8/2001 | Forster | A61B 17/1222 206/338 |
| 6,419,682 B1 | * | 7/2002 | Appleby | A61B 17/1222 206/339 |
| 6,880,699 B2 | * | 4/2005 | Gallagher | A61B 17/1222 206/339 |
| 7,198,149 B2 | * | 4/2007 | Gelardi | B65D 50/045 206/1.5 |
| 7,628,272 B2 | * | 12/2009 | Wiedenbein | A61B 17/1222 206/339 |
| 8,403,138 B2 | | 3/2013 | Weisshaupt et al. | |
| 2002/0046961 A1 | * | 4/2002 | Levinson | A61B 17/1222 206/339 |
| 2006/0124485 A1 | * | 6/2006 | Kennedy | A61B 17/1222 206/340 |
| 2009/0152147 A1 | * | 6/2009 | Cannady | A61B 17/1222 206/339 |
| 2011/0087244 A1 | | 4/2011 | Weisshaupt et al. | |

FOREIGN PATENT DOCUMENTS

| | | | | |
|---|---|---|---|---|
| CN | 1 833 615 A | | 9/2006 | |
| CN | 1833615 | | 9/2006 | |
| DE | WO 2009124576 A1 | * | 10/2009 | ........... A61B 17/122 |
| EP | 0 914 805 | | 5/1999 | |
| JP | 7-314721 | | 12/1995 | |
| JP | 2006175225 | | 7/2006 | |
| WO | 2009124576 | | 10/2009 | |

OTHER PUBLICATIONS

Korean Office action for Application No. 10-2013-7031314 dated Feb. 11, 2015.
Korean Decision of Rejection Application No. 10-2013-7031314.
Taiwanese Office action for Application No. 101114661 dated Dec. 16, 2015.
Korean Office action for Application No. 10-2013-7031314 dated Feb. 19, 2016.
European Office action for Application No. 11 864 436.8 dated Jan. 28, 2016.
Chinese Office action for Application No. 201180071875.5 dated Aug. 24, 2015.
Korean Office action for Application No. 10-2013-7031314 dated Sep. 22, 2015.
Japanese Office action for Application No. 2014-508322 dated Oct. 27, 2015.
Australian Office action for Application No. 2011366933 dated Nov. 9, 2015.
Chinese Office action for Application No. 20118007187.5 dated May 5, 2016.
Korean Office action for Application No. 10-2016-7012140 dated Jun. 1, 2016.

* cited by examiner

CARTRIDGE FOR SURGICAL FASTENERS WITH INTEGRATED LOCK SYSTEM

BACKGROUND OF THE INVENTION

The invention relates to a cartridge for surgical clips. Such cartridges are frequently used during surgical procedures to hold one or more surgical clips until they are needed by the surgeon. One issue that has been a problem in the industry is holding the clips in place in the cartridge during shipping and various handling steps prior to use in the surgical procedure.

It is the focus of the present disclosure to address this issue.

SUMMARY OF THE INVENTION

In accordance with the present invention, a cartridge for surgical clips is provided which has an integrated clip lock system which securely holds clips in place until they are to be used, and which is a simple and cost effective structure.

According to the invention, a cartridge is provided for holding surgical fasteners comprising a base having a plurality of upstanding walls, adjacent pairs of walls defining spaces for holding surgical fasteners; at least one surgical fastener securing member movably connected to the base and movable relative to the base from an open position wherein fasteners can be loaded into the spaces, and a closed position wherein fasteners in the spaces are covered and held in the spaces; and a locking structure engageable between the base and the surgical fasteners securing member for locking the surgical fastener securing member in the closed position.

In further accordance with the invention, a surgical fastener package is provided which comprises a cartridge for holding surgical fasteners, comprising a base having a plurality of upstanding walls, adjacent pairs of walls defining spaces for holding surgical fasteners; at least one surgical fastener securing member movably connected to the base and movable relative to the base from an open position wherein surgical fasteners can be loaded into the spaces, and a closed position wherein clips in the spaces are covered and held in the spaces; a locking structure engageable between the base and the surgical fastener securing member for locking the surgical fastener securing member in the closed position; a package base; an adhesive sheet between the cartridge and the package base; and a blister sheet fixed to the package base with the cartridge in the blister.

BRIEF DESCRIPTION OF THE DRAWINGS

A detailed description of preferred embodiments of the invention follows, with reference to the attached drawings, wherein.

DETAILED DESCRIPTION

The invention relates to a cartridge for holding surgical fasteners and includes an integrated surgical fastener lock system to allow efficient manufacture of the cartridge, easy loading of fasteners into the cartridge, a simple closing mechanism for securing the fasteners in the cartridge, and ease of access to the fasteners for removal when desired.

While the invention could be used with a wide variety of different types of surgical fasteners, one particularly useful application is with surgical clips which are well known to persons skilled in the art. Thus this disclosure is given in terms of surgical clips.

Figure 1:
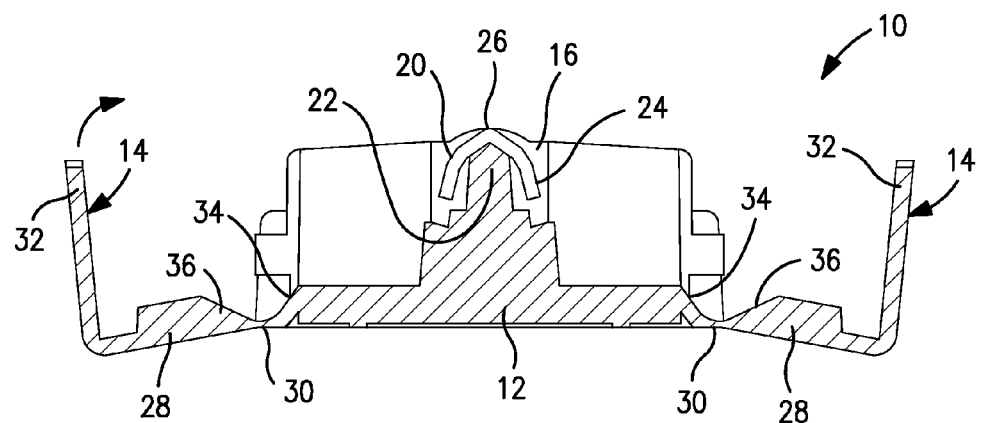
FIG. 1 is a side sectional view of a cartridge according to the invention with the surgical fastener securing member in an open position.
Figure 2:
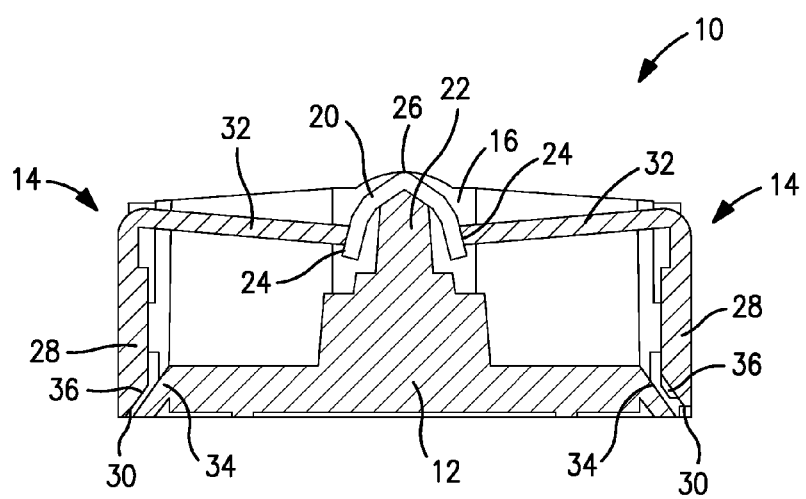
FIG. 2 is a side sectional view of a cartridge according to the invention with the surgical fastener securing member in a closed position.

FIGS. 1 and 2 are sectional views of a cartridge 10 according to the invention which includes a base 12 and clip securing members 14 movably connected to base 12 between an open position as illustrated in FIG. 1 and a closed position as illustrated in FIG. 2.

Figure 3:
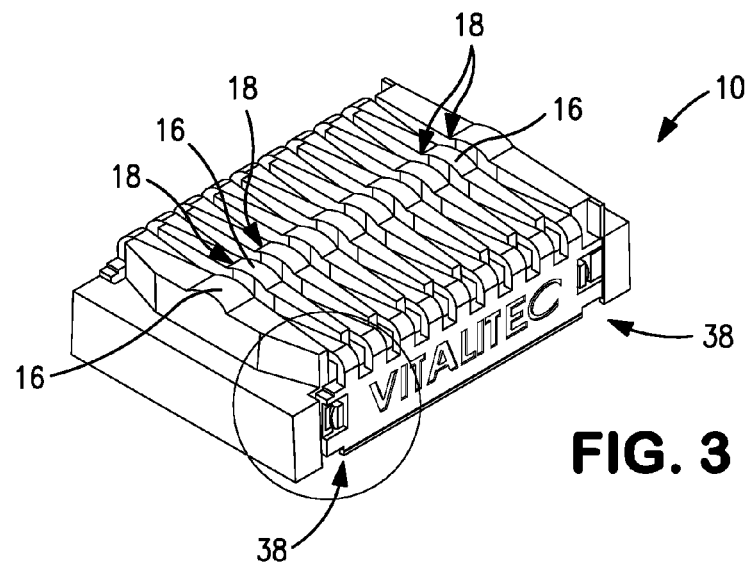
FIG. 3 is a perspective view of a cartridge according to the invention in a closed position.
Figure 4:
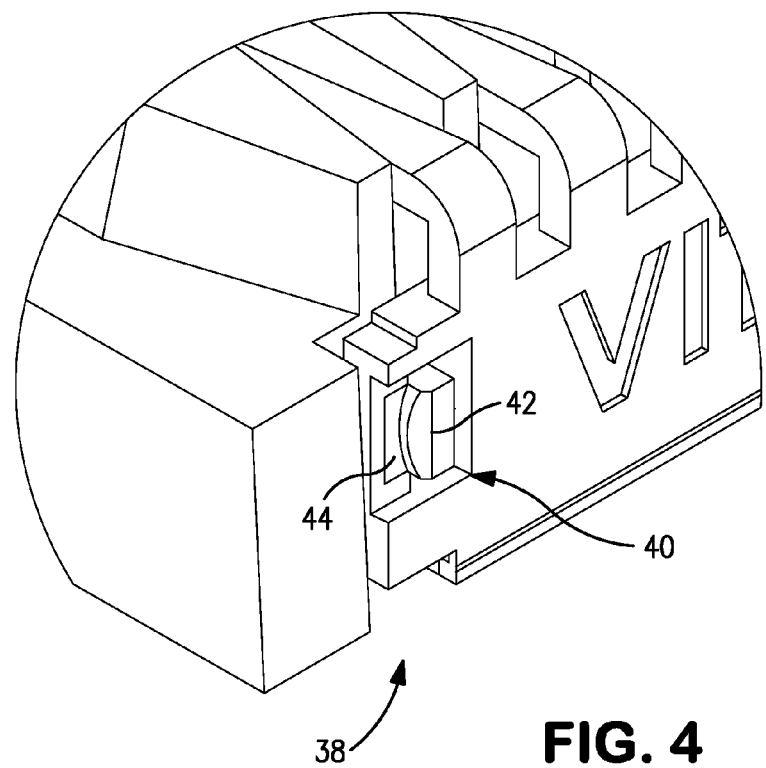
FIG. 4 is an enlarged portion of the illustration of FIG. 3 and further illustrates the integrated surgical fastener lock system of the present invention.
Figure 5:
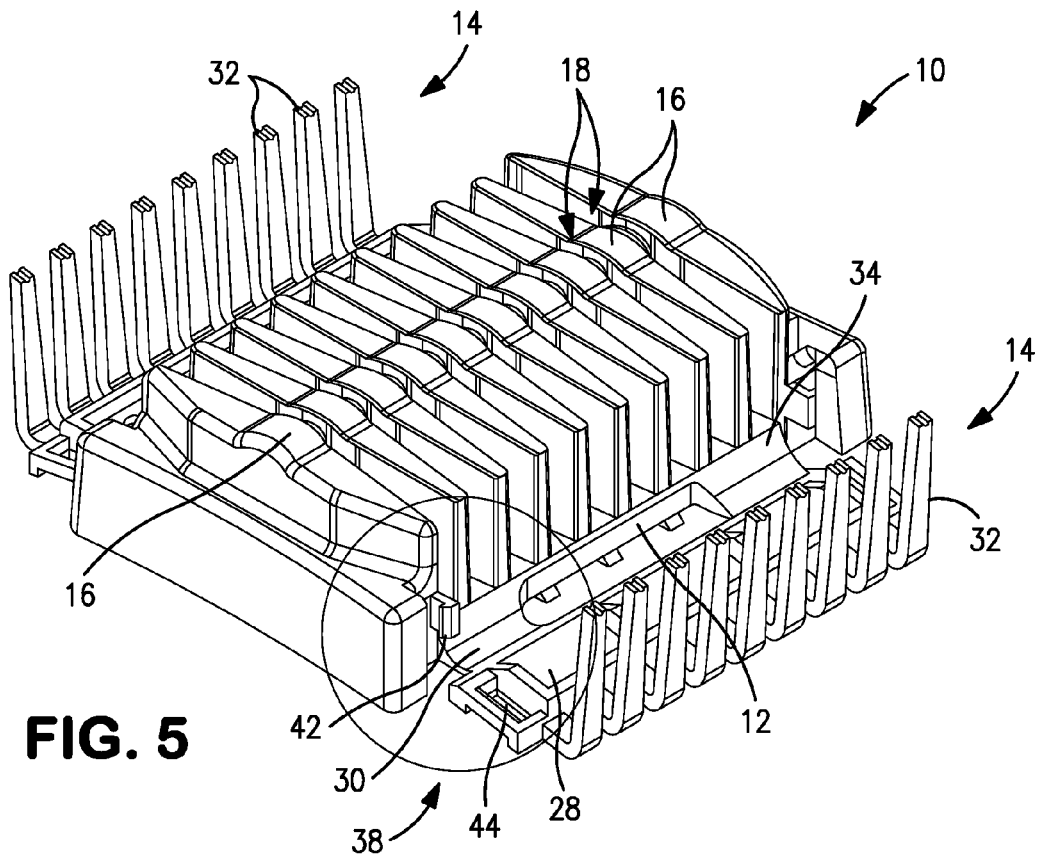
FIG. 5 shows a cartridge according to the invention with the surgical fastener securing member in an open position.
Figure 6:
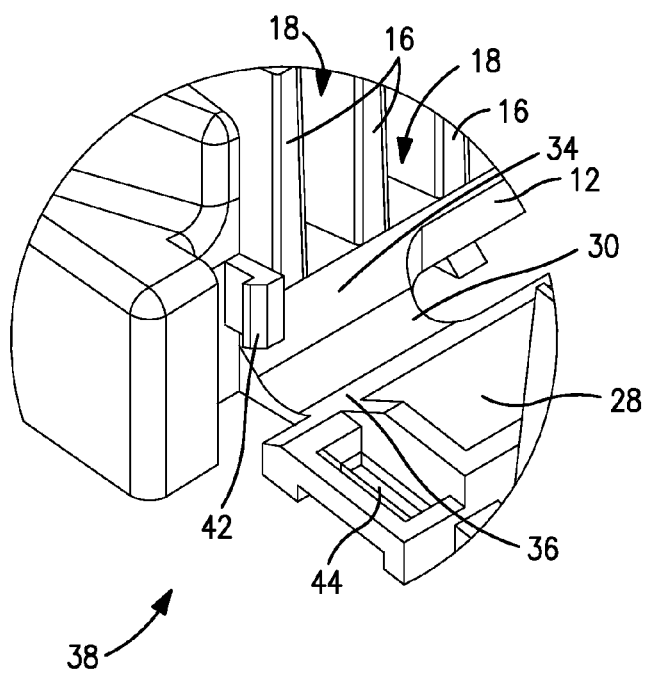
FIG. 6 is an enlarged portion of FIG. 5 showing greater detail of the integrated lock system according to the invention.

Base 12 has a plurality of upstanding walls 16 defining spaces 18 (see FIGS. 3, 5 and 7) for holding clips 20 within cartridge 10 as desired. Between walls 16, base 12 can preferably have a support 22 for holding clips 20 at the desired position within spaces 18. Support 22 can suitably match an inner shape of clip 20 to be held therein, and is further preferably shaped to allow ends 24 of a clip in space 16 to hang freely to either side of support 22.

As shown, base 12 can advantageously be a relatively square or rectangular structure having a series of substantially parallel walls 16 such that a plurality of spaces are defined for holding clips.

Figure 7:
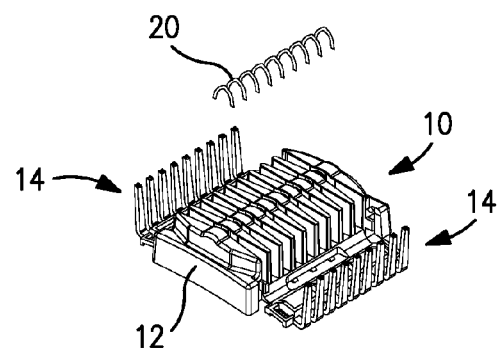
FIG. 7 shows a cartridge according to the invention in an open position with a series of clips being positioned therein.

Clip securing member 14 as set forth above is advantageously moveably connected to base 12 such that clip securing member 14 can be moved from an open position as shown in FIG. 1 to a closed position as shown in FIG. 2. When in the open position of FIG. 1, clips 20 can be positioned into spaces 18 as schematically illustrated in FIG. 7, and then clip securing member 14 can be moved to the closed position of FIG. 2 wherein the clip securing member contacts leg portions or ends 24 of clip 20, leaving the bale portion 26 exposed through the top of cartridge 10, which helps a surgeon or other qualified personnel to properly align an instrument with the clip for removing the clip from cartridge 10.

Clip securing members 14 advantageously have a side wall 28 which is moveably connected to base 12, preferably through a living hinge 30, and a flexible retaining member 32 which extends from side wall 28, preferably at an acute angle A with respect to sidewall 28, such that when sidewall 28 is in a closed position and arranged substantially perpendicular with respect to base 12, flexible retaining members 32 are at a slight incline downwardly into the space between walls 16, so that retaining members 32 can contact ends 24 of clip 20 as desired.

As indicated above, sidewall 28 of clip securing member 14 is preferably connected to base 12 through a living hinge 30 such that the desired movement of clip securing member 14 relative to base 12 is a pivot around a pivot axis defined by living hinge 30. Thus, the movement of clip securing member 14 from the open position of FIG. 1 to the closed position of FIG. 2 would be through a pivot of clip securing member 14 around a pivot axis defined by living hinge 30.

Further, base 12 and sidewall 28 advantageously have sloped surfaces 34, 36 which are in the location of connection to hinge 30, such that when clip securing member 14 is in the closed position, surfaces 34, 36 can substantially abut to provide structural strength and integrity to cartridge 10 as desired.

As set forth above, a salient aspect of the present invention is the integrated clip lock system which allows the clip securing member to be held in the closed position as desired.

FIGS. 3-6 provide further illustration of this integrated clip lock system 38. Clip lock system 38 is preferably a structure defined between base 12 and clip securing member 14 which can snap into an engaging hold of clip securing member 14 relative to base 12 when clip securing member 14 is moved to a closed position. In this regard, a latch 40 can be defined between clip securing member 14 and base 12, and latch 40 can include a flexible tab 42 defined on one of base 12 and clip securing member 14, and a receptacle 44 defined on the other of base 12 and clip securing member 14, such that flexible tab 42 snaps into and is held in receptacle 44 when clip securing member 14 is moved to the closed position. Of course, while the simple structure disclosed and shown in FIGS. 3-6 is one embodiment of a suitable latch for use in accordance with the present invention, other structures could be utilized, including the same structure with the components defined on opposite parts.

FIG. 7 shows cartridge 10 in an open position with a series of clips 20 ready for loading into cartridge 10. Cartridge 10 can be manufactured and shipped to a loading facility in an open position, and clips 20 can be loaded at the loading facility. Alternatively, clips can be loaded in line with the cartridge manufacturing process, all at a single plant. In any event, once clips are loaded into the cartridge, the clip securing member can be moved to the closed position and cartridge 10 is now ready for further packaging as shown in FIG. 8 for shipping to an ultimate user of the product.

Figure 8:
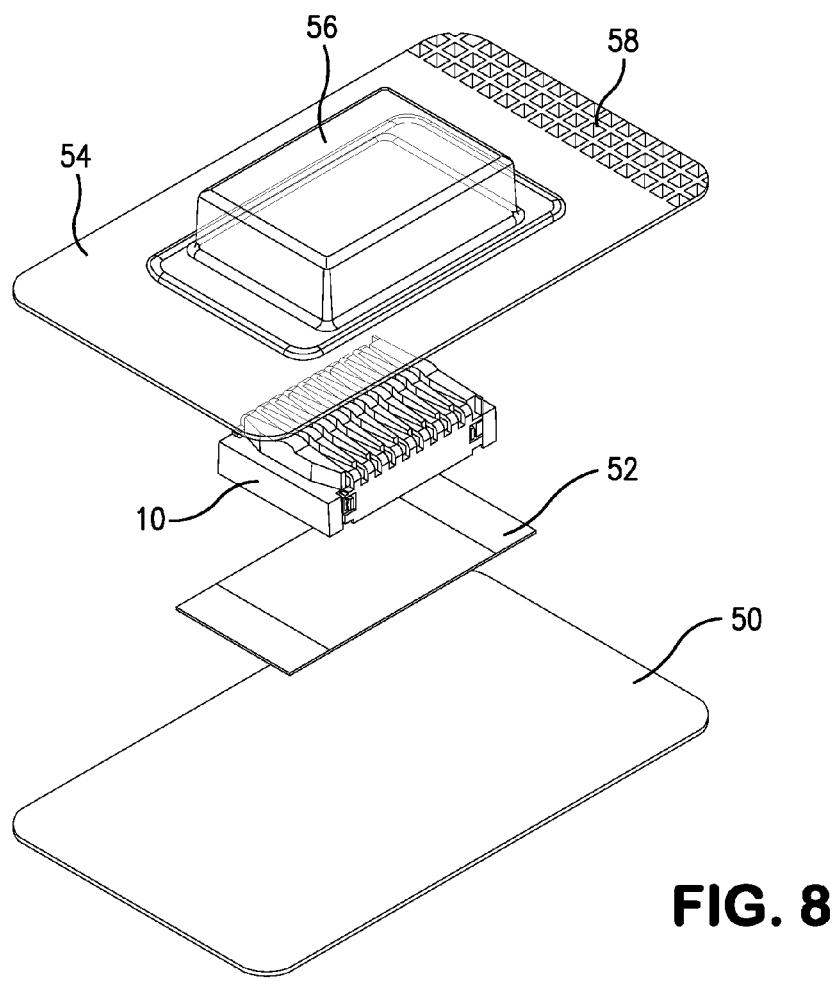
FIG. 8 shows a complete package including the cartridge according to the invention.

As shown in FIG. 8, this additional packaging can include a package base 50, a sheet of adhesive 52 between base 50 and cartridge 10, and a package top 54 including a blister 56, with package top 54 being secured to package base 50 holding cartridge 10 in blister 56 as desired.

As shown, package top 54 can have a textured and non-secured portion 58 such that the edge of the package can be separated by a user to peel package top 54 away from package base 50 and expose cartridge 10 for use. Adhesive 52 can be fixed to a bottom of cartridge 10 and have a peelable sheet for exposing adhesive 52 such that cartridge 10 can be secured to any suitable surface allowing ease of access to the surgeon during a surgical procedure.

It should be appreciated that the structure as illustrated in FIGS. 1-7 is a cartridge which can be manufactured in a single injection molding process, defining the base and clip securing members all in a single integral structure, along with the integrated clip lock system in accordance with the present invention. This greatly simplifies the loading process, and does not involve the manufacture of separate components and their handling in being placed over the cartridge base.

Clip securing members 14 are shown pivotably connected to base 10 through living hinge 30 and this is a particularly useful embodiment because it can be manufactured as a single part including the latch mechanism as well.

Alternatives could include one or more separate pieces for the clip securing member, which could have a mechanical hinge to snap into engagement with the base. The clip securing member could also be slidable relative to the base, and these embodiments fall within the broadest scope of the present invention.

Given that the disclosed cartridge is intended to be manufactured through an injection molding process, the cartridge can be manufactured from any suitable injection molded plastic such as acrylonitrile butadiene styrene (ABS), polyamide, polycarbonate and the like. Of course, other suitable materials could be used as well as other manufacturing techniques, all within the broad scope of the present invention.

It should of course be noted that the material of the cartridge should be selected to be compatible with clips to be stored therein, and further to be biocompatible such that any traces of such cartridge transferred along with a clip would not be toxic to a patient.

The above detailed description is provided to illustrate preferred embodiments of the present invention. It is of course possible to modify various structures, shapes and aspects of the invention all within the broad scope of the present invention. Thus, the embodiments disclosed are not to be seen as limiting on the scope of the invention, which is rather defined by the claims appended hereto, and equivalents thereto.

The invention claimed is:

1. A cartridge for holding surgical fasteners, comprising:
a base having a plurality of upstanding walls, adjacent pairs of walls defining spaces for holding surgical fasteners;
at least one surgical fastener securing member movably connected to the base and movable relative to the base from an open position wherein fasteners can be loaded into the spaces, and a closed position wherein fasteners in the spaces are covered and held in the spaces; and
a locking structure engageable between the base and the surgical fastener securing member for locking the surgical fastener securing member in the closed position, wherein the surgical fastener securing member comprises a sidewall pivotably mounted to the base, and a plurality of flexible retaining members which extend from the sidewall over portions of the spaces whereby fasteners can be held in the spaces and then removed when desired while the surgical fastener retaining member is in the closed position, and wherein the locking structure engages between the sidewall and the base.

2. The apparatus of claim 1, wherein the surgical fastener securing member is pivotably connected to the base, and pivotable relative to the base from the open position to the closed position.

3. The apparatus of claim 1, wherein the sidewall is connected to the base by a living hinge which defines a pivot axis for movement of the surgical fastener securing member relative to the base.

4. The apparatus of claim 3, wherein the base and the sidewall are angled leading to the living hinge to define beveled surfaces which can abut when the surgical fastener securing member is in the closed position.

5. The apparatus of claim 1, wherein the retaining member defines an acute angle with the sidewall.

6. The apparatus of claim 1, wherein the retaining member contacts a fastener in one of the spaces when the surgical fastener retaining member is in the closed position.

7. The apparatus of claim 1, wherein the surgical fastener retaining member comprises a first surgical fastener retaining member connected to one side of the base and a second surgical fastener retaining member connected to an opposite side of the base, and wherein the first and second surgical fastener retaining members combine to hold fasteners in the spaces.

8. The apparatus of claim 1, wherein the locking structure comprises a latch defined between the base and the surgical fastener securing member which engages when the surgical fastener securing member is moved to the closed position.

9. The apparatus of claim 8, wherein the latch comprises a flexible tab on one of the base and the surgical fastener securing member and a receptacle on the other of the base and the surgical fastener securing member, the flexible tab being held within the receptacle when the surgical fastener securing member is in the closed position.

10. The apparatus of claim 3, wherein the base has a bottom surface and an opposite side, with the plurality of upstanding walls extending upwardly from the opposite side, and wherein the living hinge is substantially vertically aligned with the bottom surface.

11. The apparatus of claim 5, wherein the sidewall is substantially vertical in the closed position, and wherein the plurality of flexible retaining members extend inwardly and downwardly from an upper edge of the sidewall whereby the plurality of flexible retaining members and the sidewall define the acute angle as an internal angle between the sidewall and the plurality of flexible retaining members.

* * * * *